United States Patent [19]
Mizia et al.

[11] Patent Number: 5,315,034
[45] Date of Patent: May 24, 1994

[54] PROCEDURE FOR THE PREPARATION OF ALKYL ISOCYANATES

[75] Inventors: Franco Mizia; Franco Rivetti; Ugo Romano, all of Milan, Italy

[73] Assignee: Enichem Synthesis S.p.A., Palermo, Italy

[21] Appl. No.: 60,035

[22] Filed: May 11, 1993

[30] Foreign Application Priority Data

May 15, 1992 [IT] Italy ............................ MI92A001170

[51] Int. Cl.$^5$ ........................................... C07C 263/00
[52] U.S. Cl. ................................................. 560/338
[58] Field of Search .................... 560/330, 336, 338

[56] References Cited

U.S. PATENT DOCUMENTS

| | | | |
|---|---|---|---|
| 4,596,678 | 6/1986 | Merger et al. | 560/344 CM |
| 4,613,466 | 9/1986 | Merger et al. | 560/344 |
| 5,126,480 | 6/1992 | Sofranko et al. | 560/338 |
| 5,157,155 | 10/1992 | Sakamoto et al. | 560/338 X |
| 5,189,205 | 2/1993 | McGhee et al. | 560/338 X |

FOREIGN PATENT DOCUMENTS

0323514 7/1989 European Pat. Off. .

OTHER PUBLICATIONS

Chemical Abstracts, vol. 114, No. 24, Jun. 17, 1991, "Chemistry of Synthetic High Polymers", Abstract No. 229599.

*Primary Examiner*—Arthur C. Prescott
*Attorney, Agent, or Firm*—George P. Hoare, Jr.

[57] ABSTRACT

Multistep process for the preparation of alkyl mono and diisocyanates consisting in reacting the corresponding aliphatic amine or diamine with dimethylcarbonate and, substantially, in partially vaporizing and converting the urethane thus formed in an evaporator to subsequently terminate the cracking in a II° reactor, and finally subjecting the cracking product to fractional distillation at reduced pressure, recycling the unconverted part to the partial vaporization step.

16 Claims, 1 Drawing Sheet

PROCEDURE FOR THE PREPARATION OF ALKYL ISOCYANATES

FIELD OF THE INVENTION

The present invention relates to a procedure for the preparation of alkyl mono and diisocyanates consisting in the conversion of an alkyl mono or diamine into the corresponding urethane by reaction with dialkyl carbonate and the subsequent thermal decomposition of the urethane groups into isocyanate: this procedure has the great advantage of not using toxic compounds as raw materials

BACKGROUND OF THE INVENTION

Various procedures for the preparation of isocyanates starting from aminic compounds via dialkylcarbonate are already described in literature for example, patent applications

WO 8805430; JP 2066-261; JP 2311-452 disclose a two-step procedure consisting in:
1) reacting a diamine with dimethylcarbonate in the presence of an alkaline alcoholate to produce urethane which is recovered from the mixture;
2) the decomposition of the latter at 230° C. in an organic solvent having a high boiling point in the presence of a metal and continuously removing the reaction products, by distillation.

Between 1) and 2) the catalyst is neutralized by treatment with acid, and then removed; the urethane is then purified by distillation.

This procedure has a problem in step 1) concerning the recovery of the dialkylurethane by distillation with the conventional methods, which is difficult to perform with good yields, and in step 2) various problems due to the purification of the liquid flows from the catalytic residues.

U.S. Pat. Nos. 4,596,678 and 4,596,679 also describe a two-step process consisting in:
1) reacting a diamine with urea in the presence of dialkylcarbonate and alcohol to give the corresponding alkyl diurethane;
2) subjecting the latter to partial vaporization and be then fed to a cracking reactor packed with a metallic filling with a low pressure loss which operates at a temperature which is higher than 300° C.

Between 1) and 2) the urethane, which however contains synthetic by-products, which have a negative influence on the final result, is isolated.

U.S. Pat. No. 4,613,466 discloses a one-step process wherein dialkylurethane urethane is partially vaporized without decomposition and fed as such to a cracking reactor packed with a specific metallic filling having a catalytic function.

The products are then recovered by fractional condensation.

The above two-step process has, as already mentioned, the serious disadvantage of insufficient selectivity in the synthesis of the urethane during which are formed complex mixtures which are difficult to separate; the second step of the process and also the procedure described in the last patent have problems deriving from the presence of polymeric byproducts in the alkyl diurethane, which must be removed from the vaporization chamber by the liquid current discharged (partial evaporization) and from which it is difficult to recover the alkyl diurethane. This weighs heavily on the specific consumption of the process.

SUMMARY OF THE INVENTION

The present invention consequently relates to a procedure for the preparation of alkyl mono and diisocyanates which overcomes all the disadvantages arising in the processes of the known art, and does not necessitate, as already stated, raw materials which are classified as toxic.

This procedure basically consists in the conversion of an alkyl mono or diamine into the corresponding urethane and the subsequent thermal decomposition of the urethane groups.

In particular it has been found that it is possible to obtain alkyl mono and diurethanes having a high purity with quantitive yields of the alkyl mono and diamine used, using dimethylcarbonate as a carbonylation agent in the presence of a basic catalysts selected from the alcoholates of alkaline and alkaline earth metals. These alkyl diurethanes are then fed to a cracking chamber where they undergo thermal treatment under such conditions of pressure and temperature as to allow complete vaporization and partial conversion in the useful cracking product. The mixture of vapours discharged is then fed to a subsequent cracking reactor which operates at a higher temperature and, however sufficient to make the conversion substantially complete. This stream of vapours is then subjected to fractional condensation to separate its constituents. The useful product is then recovered from the condensate stream, by distillation.

It has been found that operating with this kind of procedure it is possible to obtain alkyl mono and diisocyanates from the corresponding aminic compounds with high yields.

In accordance with the above and according to a more precise definition, the present invention relates to a procedure for the production of isocyanates having the formula:

$$R\text{—}[N=C=O]_x \quad \text{(I)}$$

wherein x represents an integer selected from 1 or 2, and R represents an alkyl radical with a number of carbon atoms of up to 10, either linear or branched, simple or having substituents selected from alkoxy groups, halogen or cycloalkyl radicals; or a cycloalkyl radical with a number of carbon atoms of between 5 and 7, again either simple or having substituents selected from those specified above, a procedure which includes the following steps:

a) reaction of an amine having the formula $$R\text{—}[NH_2]_x \quad \text{(IV)}$$

with dimethylcarbonate in the presence of a basic catalyst selected from the alcoholates of alkaline or alkaline-earth metals to give methylurethanes having the formula $$R\text{+}[NHCOOMe]_x \quad \text{(II)}$$

according to the reaction

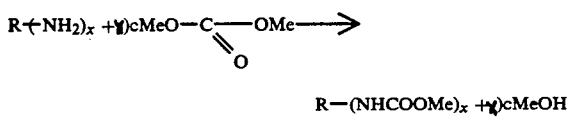

R—(NHCOOMe)$_x$ +$_x$cMeOH with x and R which have the above-defined meanings;

b) neutralization of the basic catalyst;
c) removal of the alcohol and any excess of dimethylcarbonate;
d) vaporization with partial cracking of the methylurethane obtained in step a);
e) exhaustive cracking of the urethane;
f) fractional distillation at reduced pressure of the cracking products with possible recycling of to the unconverted part in step d).

Isocyanates which can be advantageously obtained according to the procedure of the present invention are butylisocyanate, cyclohexylisocyanate, hexamethylendiisocyanate and isophoronediisocyanate.

The procedure of the present invention may be described in further detail as follows:

in a first step the dimethyl carbonate is reacted with the amine in continuous or batch in a molar ratio of between 1/1 and 10/1 and in the presence of the catalyst in quantities of between 0.01 and 0.15 moles per amino equivalent to be reacted. Particularly suitable catalysts are the sodium alcoholates derived from $C_1$–$C_4$ linear or branched alcohols: above all, sodium methoxide. The reaction is carried out within a temperature of 40° to 90° C. for a period of time ranging from 0.2 to 4 hours.

In accordance with this there is a complete or substantially complete conversion of the amino groups to form a mixture of urethane and methanol according to the above reaction.

The catalyst is neutralized, preferably maintaining the reaction temperature, by treatment with an organic or inorganic acid, in the homogeneous or heterogeneous phase, of the reacted mixture. Acids which can be used for the purpose are preferably the mono and dicarboxylic acids, the alkyl or aryl sulphonic acids also in the form of ion-exchange resins and the phosphoric acid. The urethane is recovered by removing the alcohol and possible excess of carbonate by distillation with a pressure ranging from 200 to 760 mm Hg and boiler temperature of between 40° and 140° C.;

in a second reaction step the liquid urethane either pure or in solution with a high-boiling solvent in a weight ratio of the latter with respect to the urethane of between 1/1 and 0.1/1, is fed into a cracking chamber. In a preferred embodiment a recycled current is also fed from the third step as described later.

This cracking chamber is fed with a LHSV space velocity of between 1 and 6 hr$^{-1}$, and operates within a temperature range of 150° to 300° C. and a pressure of between 0.5 and 760 mmHg.

The mixture of vapours obtained is continuously fed to a second cracking chamber with a GHSV space velocity rate of between 10 and 100 hr$^{-1}$, maintaining it conveniently in equipressure with the previous chamber and with a temperature range of 300° to 600° C.

In accordance with this there is a complete conversion of the urethane to isocyanate mixed with alcohol and also possibly with an intermediate which can be formed when x is 2, according to the following equations:

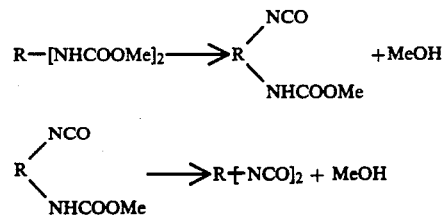

This mixture of vapours is then subjected to fractional condensation obtaining within a temperature range of 50° to 120° C., a liquid fraction basically containing the final product possibly mixed with the above intermediate. If desired a second liquid fraction can be obtained within a temperature range of −40° to +20° C. basically containing methanol.

in a third step of the procedure the flow of condensate containing an abundance of the useful product is fed continuously or semi-continuously to a distillation apparatus composed of a boiler equipped with a column. This apparatus generally operates with a brief contact time and at a reduced pressure which causes the condensation of isocyante vapours (I) in a temperature range of between 10° and 150° C.

In accordance with this a stream of condensed vapours is obtained from the head of the column, in a typical weight ratio with the feeding of between 0.5/1 and 0.8/1, mainly composed of the useful product with a purity which is higher than 99.5% parts by weight. From the bottom of the column a residue liquid flow is obtained composed of isocyanate possibly mixed with the intermediate which is formed when x corresponds to two. This stream, as already specified, in a preferred embodiment is recycled as a liquid to the first cracking chamber (second step).

The embodiment herein described affords a useful product with particularly high yields because the vaporization under cracking conditions starting from high purity urethanes a produces isocyanates with an unexpected improved selectivity with respect to the procedures of the known art. In addition, the embodiment herein described enables the isocyanates to be recovered and purified without the use of diluents and without the formation of polymeric by-products owing to the combination of benefits deriving from distillation at reduced pressure and those deriving from a reduction of the contact times.

The following is a detailed description of an embodiment or example of the invention, but the illustrative embodiment or example is not intended to and does not limit the present invention to the specific embodiment or example presented.

Figure 1:
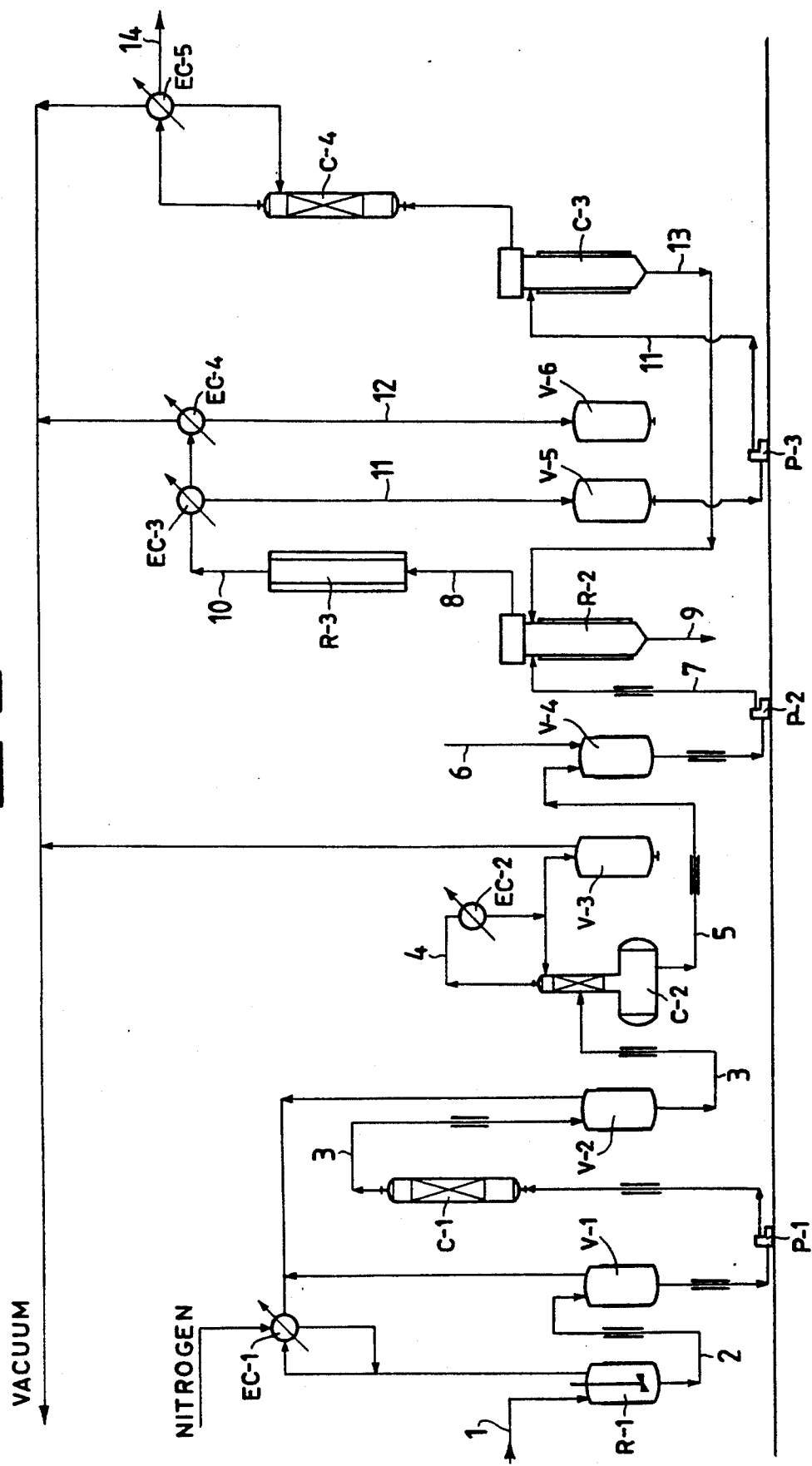
FIG. 1 schematically illustrates an embodiment of the equipment which can be used in carrying out the present invention.

Referring to the drawing, the first step of the procedure is carried out in
the equipment composed of: R1, C1, C2, V1, V2, V3, EC-1, EC-2 and P1.

The condensers EC-1 and EC-2 are brought to an operating temperature of about 15°-20° C.

102.8 parts by weight of anhydrous (50 ppm max of water) dimethylcarbonate (hereinafter referred to as DMC) and 0.3 parts of sodium methoxide (hereinafter referred to as CH₃ONa) in a 30% p. solution of methanol are charged into the reactor R1 at atmospheric pressure.

R1 is heated to 65° C., then 33.1 parts of liquid hexamethylendiamine (hereinafter referred to as HDA) kept under nitrogen are fed in portions. At the end of the reaction a flow (2) is fed to V1 (conditioned at 65° C.), consisting of 136.0 parts composed of:

48.7% bw of bis-N (1.6) hexamethylene O-methyl urethane (hereinafter referred to as HDU)
37% bw of DMC
14.1% bw of methanol and
0.22 bw of CH₃ONa The neutralization of CH₃ONa is carried out in the dehydrated and conditioned column C1 which contains a bed of resin with sulphonic ion-exchange of which the concentration of acidic hydrogen ions is known such as for example Amberlyst-15 (spherical particles) (supplied by ROHM and HAAS).

The flow (2) is volumetrically fed from V1 to C1, conditioned at 65° C., with a volumetric rate equal to 1 volume of bed per hour. A liquid flow (3) is obtained from C1 in a weight ratio with (2) equal to 0.99/1 containing:

49% p HDU, 37% p DMC, 14% p methanol with a residue content of sodium lower than 0.3 ppm. This flow (3) is collected in V2 suitably thermostat-regulated at 65° C.

The HDU is isolated in the batch column C2 for the vaporization of DMC and methanol. The above-mentioned flow (3) is fed from V2 to C2, initially at 65° C., the temperature of the bottom is then gradually brought, at atmospheric pressure, to a maximum of 140° C. and these conditions are left until the vapours have been exhausted eventually completing by decreasing the pressure to 400 mmHg.

68.7 parts of a stream of vapours (4) are obtained from C2, which is condensed in EC-2 and collected in V3, composed of:

72.5% p of DMC, 27.5% p of methanol.

66.0 parts of a bottom liquid stream (5) of HDU having a purity higher than 99.5% parts by weight with a content of residuous sodium lower than 0.5 ppm are also obtained from C2 and collected in V4.

From the above data a yield of HDU based on HDA equal to 99.7% can be calculated for the first step.

The second step of the procedure is carried out in equipment composed of: R2, R3, C3, C4, EC-3, EC-4, V4, V5, V6 and P2.

The reactor R2 is composed of a thin film evaporator, reactor R3 is tubular with a length of 1500 mm and internal diameter of 24.8 mm. This reactor is made of AISI 316L steel and is packed with a low pressure loss packing of the same material in the form of flakes.

EC-3 is brought to +60° C. and EC-4 to −20° C., the system of reactors R2 and R3 is brought to a value of residual pressure equal to 75 mmHg measured at the outlet of R2; R2 is heated to 290° C. and R3 to 420° C. Under these conditions 66 parts of a flow (7) composed of liquid HDU having a purity greater than 99.5% with and a content of sodium residue lower than 0.5 ppm, are fed from V4 to R2 with an LHSV space velocity of 1.4 hr⁻¹. 64 parts of a gaseous flow (8) are removed from R2, containing:

3.34% bw of methanol;
1.36% bw of hexamethylendiisocyanate (hereinafter HDI);
17.6% bw of hexamethylene monourethane monoisocyanate (hereinafter HMI);
77.34% bw of HDU.

2.32 parts of a liquid stream (9) having the following composition are also taken from R2:

57.7% bw HDU and
42.2% bw of polymeric by-products (polyureas).

As already mentioned 64 parts of the stream of vapours (8) already described are fed from R2 to R3 with a GHSV space velocity equal to 38 hr⁻¹. 64 parts of a stream of vapours (10) containing the following are taken from R3:

67.23% bw HDI;
5.98% bw HMI and
26.6% bw of methanol which is partially condensed in EC-3. 46.5 parts of a liquid stream (11) containing the following are obtained from EC-3:

91.6% bw HDI and
8.17% bw HMI which is collected in V5. 16.8 parts of a gaseous stream (12) containing mainly methanol are also obtained from EC-3 which is subsequently condensed in EC-4 and collected in V6.

From the above data a conversion of HDU of 97.9%, a selectivity to HDI of 91.0% and a selectivity to HMI of 6.8% are calculated for the second step.

The third step of the procedure is carried out in equipment composed of C3, C4, EC-5 and P3.

Column C3 is composed of a falling-film evaporator, column C4 is a distillation column of the conventional packed type.

The condenser EC-5 is brought to 20° C. Columns C3 and C4 are brought to a residual pressure value of 5 mmHg measured at the head of C4, C3 is heated to 131° C.

Under these conditions 46.5 parts of the liquid flow (11) already described are fed from V5 to C3 with a flow rate related to the exchange surface of 3 kg×hr⁻¹×m⁻².

32.9 parts of a stream of vapours (14), taken from C4 and condensed in EC-5, are composed of the product HDI with a purity higher than 99.5% by weight. 13.6 parts of a liquid flow (13) having the following composition are taken from C3:

71.1% bw HDI,
27.8% bw HMI which as already specified in the preferred embodiment is subsequently fed to reactor R2 of the second step.

From the above data a mass balance of HDI equal to 100% and a molar balance of HMI equal to 100% are calculated for the third step. The recovery yield of HDI is equal to 77% per passage.

We claim:

1. Procedure for the preparation of alkyl mono and diisocyanates having the formula:

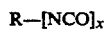

R—[NCO]$_x$ wherein x represents an integer selected from 1 or 2, and R represents an alkyl radical with a number of carbon atoms of up to ten, either linear or branched, simple or having substituents selected from alkoxy groups, halogens or cycloalkyl radicals; or a cycloalkyl radical with a number of carbon atoms of between 5 and 7, again either simple or having substituents selected from those specified above, which includes the following operations:

a) reaction of an amine having the formula

with dimethylcarbonate in the presence of a basic catalyst
b) neutralization of the basic catalyst;
c) removal of the alcohol formed and any excess of dimethylcarbonate;
d) vaporization with partial cracking of the urethane obtained in step a);
e) exhaustive cracking of the urethane obtained in step d);
f) fractional distillation at reduced pressure of the cracking product obtained in step e).

2. Procedure for the preparation of alkyl mono and diisocyanates according to claim 1 wherein the reaction in step a) takes place in the presence of a catalyst selected from the alcoholates of alkaline or alkaline-earth metals.

3. Procedure for the preparation of alkyl mono and diisocyanates according to claim 2 wherein the reaction takes place in the presence of sodium methoxide.

4. Procedure for the preparation of alkyl mono and diisocyanates according to claim, 2 wherein the reaction takes place in the presence of a quantity of catalyst of between 0.01 and 0.15 moles per mole of amine.

5. Procedure for the preparation of alkyl mono and diisocyanates according to claim 1 wherein the reaction of step a) is carried out at a temperature ranging from 40° to 90° C.

6. Procedure for the preparation of alkyl mono and diisocyanates according to claim 1 wherein the reaction of step a) is carried out with a molar ratio between the dimethylcarbonate and the amine of between 1/1 and 10/1.

7. Procedure for the preparation of alkyl mono and diisocyanates according to claim wherein the vaporization with partial cracking in step d) is carried out at a temperature ranging from 150° to 300° C.

8. Procedure for the preparation of alkyl mono and diisocyanates according to claim 1 wherein the vaporization with partial cracking of step d) is carried out within a pressure range of 0.5 to 760 mmHg.

9. Procedure for the preparation of alkyl mono and diisocyanates according to claim 1 wherein the vaporization with partial cracking of step d) is carried out in a thin-film evaporator.

10. Procedure for the preparation of alkyl mono and diisocyanates according to claim 1 wherein the exhaustive cracking in step e) is carried out at a temperature ranging from 300° to 600° C.

11. Procedure for the preparation of alkyl mono and diisocyanates according to claim 1 wherein the exhaustive cracking of step e) is carried out in a tubular reactor.

12. Procedure for the preparation of alkyl mono and diisocyanates according to claim 1 wherein the fractional distillation in step f) is carried out at a temperature ranging from 10° to 150° C.

13. Procedure for the preparation of alkyl mono and diisocyanates according to claim 1 wherein the fractional distillation of step f) is carried out in a thin-film evaporator whose vapours are fed into a distillation column.

14. Procedure for the preparation of alkyl mono and diisocyanates according to claim 1 wherein the vaporization with partial cracking of step d) is carried out by feeding the urethane obtained in step 2) in solution of a high-boiling solvent to the evaporator in a weight ratio of between 1/1 and 0.1/1.

15. Procedure for the preparation of alkyl mono and diisocyanates according to claim 1 wherein the neutralization of the basic catalyst of step b) is carried out by treatment with an organic or inorganic acid, in a homogeneous or heterogeneous phase.

16. Procedure for the preparation of alkyl mono and diisocyanates according to claim 1, wherein the unconverted part from step f) is recycled to step d).

* * * * *